(12) United States Patent
Kim et al.

(10) Patent No.: US 11,426,084 B2
(45) Date of Patent: Aug. 30, 2022

(54) METHOD, APPARATUS AND COMPUTER PROGRAM FOR NONINVASIVELY DETERMINING CAUSE OF BLOOD PRESSURE CHANGE

(71) Applicants: THE ASAN FOUNDATION, Seoul (KR); UNIVERSITY OF ULSAN FOUNDATION FOR INDUSTRY COOPERATION, Ulsan (KR)

(72) Inventors: Sung Hoon Kim, Seoul (KR); Young Jin Moon, Seoul (KR); Gyu Sam Hwang, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 414 days.

(21) Appl. No.: 16/698,886

(22) Filed: Nov. 27, 2019

(65) Prior Publication Data
US 2020/0093376 A1  Mar. 26, 2020

Related U.S. Application Data

(63) Continuation of application No. PCT/KR2018/007050, filed on Jun. 22, 2018.

(30) Foreign Application Priority Data

Jun. 23, 2017 (KR) .................. 10-2017-0079931

(51) Int. Cl.
*A61B 5/021* (2006.01)
*A61B 5/00* (2006.01)
(Continued)

(52) U.S. Cl.
CPC ............ *A61B 5/021* (2013.01); *A61B 5/7203* (2013.01); *A61B 5/7225* (2013.01);
(Continued)

(58) Field of Classification Search
CPC ..... A61B 5/021; A61B 5/7203; A61B 5/7225; A61B 5/7278; A61B 5/023; A61B 5/04
See application file for complete search history.

(56) References Cited

U.S. PATENT DOCUMENTS

2002/0082508 A1* 6/2002 Ogura ................ A61B 5/02125
600/490
2007/0021786 A1* 1/2007 Parnis ................ A61N 1/36114
607/2
(Continued)

FOREIGN PATENT DOCUMENTS

CN      101518439 A    9/2009
JP      2009-521260 A  6/2009
(Continued)

OTHER PUBLICATIONS

International Search Report issued in PCT/KR2018/007050; dated Sep. 3, 2018.

*Primary Examiner* — Catherine M Voorhees
*Assistant Examiner* — Roland Dinga
(74) *Attorney, Agent, or Firm* — Studebaker & Brackett PC

(57) ABSTRACT

The present disclosure relates to a method, an apparatus and a computer program for noninvasively determining a cause of a blood pressure change. The method includes at least: obtaining maximum amplitudes of heart sounds; monitoring changes in the maximum amplitudes; estimating change amounts of indexes on a myocardial contractile force and on vascular resistance, based on increasing or decreasing of a blood pressure of the patient, and the changes in the maximum amplitudes; and determining the cause of the blood
(Continued)

pressure change of the patient as an effect of at least one of alpha action, alpha blockage, beta action and beta blockage, based on results of the estimation of the first change amount of the first index, the second change amount of the second index and the third change amount of the third index.

13 Claims, 7 Drawing Sheets

(51) Int. Cl.
      *A61B 7/02*       (2006.01)
      *A61B 7/04*       (2006.01)

(52) U.S. Cl.
      CPC ............ *A61B 5/7278* (2013.01); *A61B 7/023* (2013.01); *A61B 7/04* (2013.01)

(56) References Cited

U.S. PATENT DOCUMENTS

| | | | |
|---|---|---|---|
| 2012/0112903 A1 | 5/2012 | Kaib et al. | |
| 2013/0158417 A1* | 6/2013 | Borger | A61B 5/0225 600/485 |
| 2016/0120416 A1* | 5/2016 | Kim | A61B 7/023 600/528 |

FOREIGN PATENT DOCUMENTS

| | | |
|---|---|---|
| KR | 10-2006-0088770 A | 8/2006 |
| KR | 10-2011-0013153 A | 2/2011 |
| KR | 10-1072455 B1 | 10/2011 |
| KR | 10-2016-0053395 A | 5/2016 |

\* cited by examiner

METHOD, APPARATUS AND COMPUTER PROGRAM FOR NONINVASIVELY DETERMINING CAUSE OF BLOOD PRESSURE CHANGE

CROSS-REFERENCE TO RELATED APPLICATIONS

The present application is a continuation of International Patent Application No. PCT/KR2018/007050, filed Jun. 22, 2018, which is based upon and claims the benefit of priority to Korean Patent Application No. 10-2017-0079931, filed on Jun. 23, 2017. The disclosures of the above-listed applications are hereby incorporated by reference herein in their entirety.

BACKGROUND

Embodiments of the inventive concept described herein relate to a method of evaluating a cardiovascular function, and more particularly, relate to a method, an apparatus and a computer program for noninvasively determining a cause of a blood pressure change based on the heart sounds of a patient.

Vasoactive drugs exhibit various physiological effects, and even if they superficially show the same phenomenon (e.g., an increase in blood pressure), the underlying physiological effects may be different (e.g., an increase in peripheral blood vessel resistance or an increase in myocardial contractility).

In the state of invasive hemodynamic monitoring, when alpha and beta agonists are administered, as the systolic peak valve ring speed (S'), hourly ventricular pressure change rate (dp/dt) and systemic vascular resistance (SVR) increase together with the blood pressure, the dose effect may be quantitatively confirmed. When an alpha agonist is administered, the SVR and dp/dt increase simultaneously with an increase in blood pressure, but the S' does not change significantly. When a beta blocker is administered, dp/dt and S' decrease simultaneously with a slight drop in blood pressure, but SVR does not change significantly.

Accordingly, in a conventional clinic, the quantitative effects of alpha agonists/blockers and beta agonists/blockers are evaluated by simultaneously observing and comprehensively analyzing changes in indexes such as S', dp/dt, and SVR.

However, because invasive arterial pressure measuring equipment, a swan-ganz catheter and echocardiography equipment, and the like are required to observe the change of the indexes, and also because it is an invasive test method, it is difficult in reality to simultaneously monitor changes in the indexes in a clinic, despite its necessity.

In addition, even when observing and analyzing the changes of the indexes at the same time, it is impossible to quickly identify and cope with the cause of blood pressure change because an arterial tube and a swan-ganz catheter should be inserted. Even if the symptoms of blood pressure changes are the same, it is very important to quickly identify the cause of the blood pressure change because the treatment policy varies depending on the cause.

SUMMARY

Embodiments of the inventive concept provide a method, an apparatus and a computer program for noninvasively determining a cause of a blood pressure change.

Objects of the inventive concept may not be limited to the above, and other objects will be clearly understandable to those having ordinary skill in the art from the following disclosures.

According to some embodiments, a method for noninvasively determining a cause of a blood pressure change, performed by a computer including a processor, includes: obtaining heart sounds of a patient; obtaining a first maximum amplitude of a first heart sound and a second maximum amplitude of a second heart sound, from the obtained heart sounds; monitoring a first change in the first maximum amplitude and a second change in the second maximum amplitude; estimating a first change amount of a first index on a myocardial contractile force, a second change amount of a second index on the myocardial contractile force, and a third change amount of a third index on vascular resistance, based on increasing or decreasing of a blood pressure of the patient, a first change amount of the first maximum amplitude, and a second change amount of the second maximum amplitude of the second heart sound; and determining the cause of the blood pressure change of the patient as an effect of at least one of alpha action, alpha blockage, beta action and beta blockage, based on results of the estimation of the first change amount of the first index, the second change amount of the second index and the third change amount of the third index. In these embodiments, the first heart sound corresponds to a closed sound of a mitral valve or a tricuspid valve, and the second heart sound corresponds to a closed sound of an aortic valve or a pulmonary valve.

According to some other embodiments, an apparatus for performing a method for noninvasively determining a cause of a blood pressure change, includes: an input port configured to receive heart sounds; a processor configured to perform operations including: obtaining a first maximum amplitude of a first heart sound and a second maximum amplitude of a second heart sound, from the received heart sounds; monitoring a first change in the first maximum amplitude and a second change in the second maximum amplitude; estimating a first change amount of a first index on a myocardial contractile force, a second change amount of a second index on the myocardial contractile force, and a third change amount of a third index on vascular resistance, based on increasing or decreasing of a blood pressure of the patient, a first change amount of the first maximum amplitude, and a second change amount of the second maximum amplitude of the second heart sound; and determining the cause of the blood pressure change of the patient as an effect of at least one of alpha action, alpha blockage, beta action and beta blockage, based on results of the estimation of the first change amount of the first index, the second change amount of the second index and the third change amount of the third index, a memory configured to store instructions for performing the operations by the processor; and an output port configured to output information about the determined cause of the blood pressure change. In these embodiments, the first heart sound corresponds to a closed sound of a mitral valve or a tricuspid valve, and the second heart sound corresponds to a closed sound of an aortic valve or a pulmonary valve.

According to some other embodiments, a computer program, which is coupled to a processor and stored in a medium, includes instructions for performing: obtaining heart sounds of a patient; obtaining a first maximum amplitude of a first heart sound and a second maximum amplitude of a second heart sound, from the obtained heart sounds; monitoring a first change in the first maximum amplitude and a second change in the second maximum amplitude;

estimating a first change amount of a first index on a myocardial contractile force, a second change amount of a second index on the myocardial contractile force, and a third change amount of a third index on vascular resistance, based on increasing or decreasing of a blood pressure of the patient, a first change amount of the first maximum amplitude, and a second change amount of the second maximum amplitude of the second heart sound; and determining the cause of the blood pressure change of the patient as an effect of at least one of alpha action, alpha blockage, beta action and beta blockage, based on results of the estimation of the first change amount of the first index, the second change amount of the second index and the third change amount of the third index. In these embodiments, the first heart sound corresponds to a closed sound of a mitral valve or a tricuspid valve, and the second heart sound corresponds to a closed sound of an aortic valve or a pulmonary valve.

Other specific details of the inventive concept are included in the detailed description and drawings.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 2 is a diagram illustrating hemodynamic variables S1a and S2a;

DETAILED DESCRIPTION

Figure 1:
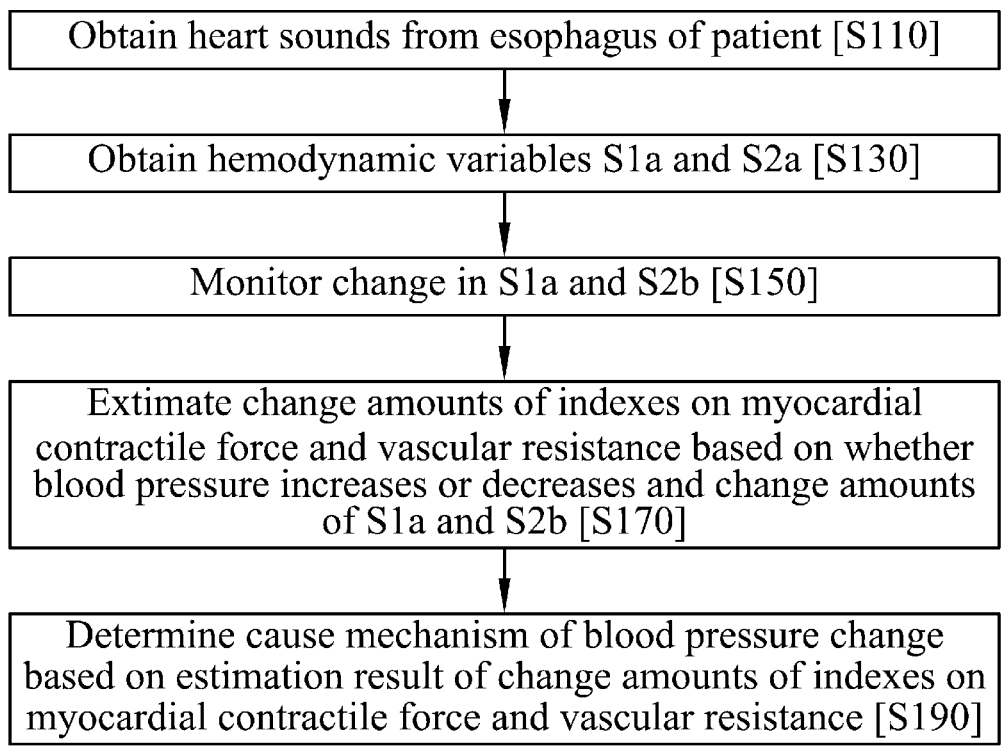
FIG. 1 is a flowchart illustrating a method of noninvasively determining a cause of a blood pressure change according to some embodiments of the present disclosure.

Advantages and features of embodiments of the inventive concept, and method for achieving them will be apparent with reference to the accompanying drawings and detailed description that follows. But, it should be understood that the inventive concept is not limited to the following embodiments and may be embodied in different ways, and that the embodiments are given to provide complete disclosure of the inventive concept and to provide thorough understanding of the inventive concept to those skilled in the art, and the scope of the inventive concept is limited only by the accompanying claims and equivalents thereof.

The terms used in the present disclosure are provided to describe embodiments, not intended to limit the inventive concept. In the present disclosure, singular forms are intended to include plural forms unless the context clearly indicates otherwise. It will be further understood that the terms "comprises," and/or "comprising," used herein, specify the presence of stated elements, but do not preclude the presence or addition of one or more other elements. In the present disclosure, like reference numerals indicate like elements, and the term "and/or" indicates each of the listed components or various combinations thereof. Terms, such as "first," "second," and the like, are for discriminating various components. However, the scope is not limited to the above terms. The above terms are used for discriminating one component from another component. Therefore, the first component mentioned below may be the second component within the technical spirit of the inventive concept.

Unless otherwise defined, all terms used herein (including technical or scientific terms) have the same meanings as those generally understood by those ordinarily skilled in the art to which the inventive concept pertains. Such terms as those defined in a generally used dictionary are not to be interpreted as having ideal or excessively formal meanings unless defined clearly and specifically.

In the present disclosure, S1a and S2a mean the first maximum amplitude of a first heart sound S1 and the second maximum amplitude of a second heart sound S2, respectively.

Systolic peak valve ring speed (S') refers to a maximum speed of blood flow through a systolic valve ring. Ventricular pressure change rate per hours (dp/dt) refers to an instantaneous rate of change of left ventricular pressure per hour. Systemic vascular resistance (SVR) refers to a resistance to blood flow ejected from a left ventricle. Systolic blood pressure (SBP) refers to pressure applied on systolic blood vessels. R-R peak Interval (RRI) refers to an interval between R wavelengths in an electrocardiogram.

In the present disclosure, an alpha agonist means a drug (e.g., phenylephrine, phenylpropanolamine, and the like) that selectively stimulates an alpha receptor without acting on a beta receptor. An alpha blocker refers to a drug (e.g., phentolamine, tolazoline, phenoxybenzamine, and the like) that blocks the action of neurotransmitters at the alpha receptor. A beta agonist refers to a drug (e.g., isoprenaline, and the like) that selectively stimulates a beta receptor without acting on an alpha receptor. A beta blocker refers to a drug (e.g., esmolol, propranolol, and the like) that blocks the action of a neurotransmitter at the beta receptor.

In addition, an alpha action effect means an action effect according to the stimulation of the alpha receptor. An alpha blocking effect means the effect of blocking the action of neurotransmitters at the alpha receptor. A beta action effect refers to an action effect of beta receptor stimulation. A beta blocking effect refers to an effect of blocking the action of neurotransmitters at a beta receptor.

Hereinafter, embodiments of the inventive concept will be described in detail with reference to the accompanying drawings.

FIG. 1 is a flowchart illustrating a method of noninvasively determining a cause of a blood pressure change according to some embodiments of the present disclosure.

Referring to FIG. 1, a method of noninvasively determining a cause of a blood pressure change according to some embodiments includes operation S110 of obtaining heart sounds from the esophagus of the patient, an operation S130 of obtaining hemodynamic variables S1a and S2a from the heart sounds, an operation S150 of monitoring changes in S1a and S2a, an operation S170 of estimating the change amounts of first and second indexes on myocardial contractile force and the change amount of a third index on vascular resistance, based on increasing or decreasing of the blood pressure of a patient, and the change amounts of S1a and S2a, and an operation S190 of determining a cause of the blood pressure change of the patient based on the estimation result of the change amounts of the first to third indexes.

In operation S110, heart sounds according to some embodiments are obtained from a stethoscope inserted into the esophagus of a patient. In detail, in order to obtain heart sounds, an intra-esophageal stethoscope may be used. By the intra-esophageal stethoscope, the hard heart sounds of the patient are obtained. Meanwhile, the heart sounds of the patient may be obtained through other body parts (such as a chest surface) other than the esophagus. In addition, the heart sound of the patient may be obtained through the processing of other types of acoustic signals obtained from the patient. The scheme of obtaining the heart sound of a patient is not limited to the illustrated schemes.

In some embodiments, the obtained heart sounds are divided into a first heart sound and a second heart sound. As described below, the first and second heart sounds correspond to the closed sounds of the atrioventricular valve (i.e., the tricuspid valve or the mitral valve) and the semilunar valve (aortic valve or pulmonary valve), respectively.

Meanwhile, in some embodiments, an operation of amplifying and analog-to-digital converting the heart sound signals are further included in a method of the present disclosure. In addition, in some embodiments, a filter is applied to the digitally converted heart sound data for the purpose of noise removal. For example, a 5-th order band pass filter of 10 to 100 Hz and/or a 10-Hz low pass filter are applied, but the embodiments are not limited thereto.

In some embodiments, a phonocardiogram (PCG) is used as the heart sound signal, but the embodiments are not limited thereto.

In operation S130, hemodynamic variable S1a is derived from the first heart sound and hemodynamic variable S2a is derived from the second heart sound. A scheme of obtaining hemodynamic variables S1a and S2a will be described in detail later with reference to FIG. 2.

In operation S150, the relative change amounts of S1a and S2a are monitored. To this end, in some embodiments, the waveform of the first heart sound signal is converted into an absolute vale and the highest point of the converted waveform is extracted. The first and second heart sound signals may be normalized based on the highest point of 100%. By the normalization, the relative change amounts of S1a and S2a may be monitored in percentage.

In operation S170, the first index on myocardial contractility is the systolic peak valve ring speed (S'), and the second index is the rate of ventricular pressure change per hour (dp/dt). In addition, the third index on vascular resistance is a systemic vascular resistance (SVR). When the blood pressure of the patient increases or decreases, a scheme of estimating the change amounts of S', dp/dt and SVR based on the change amounts of S1a and S2a will be described in detail with reference to FIGS. 3 and 4.

In operation S190, the cause of the blood pressure change of the patient is determined based on the estimation results of the change amounts of S', dp/dt and SVR. In some embodiments, the cause of the blood pressure change of the patient is classified into effects of an alpha action, an alpha blockage, a beta action, a beta blockage, and the like. That is, as the alpha receptor is selectively stimulated, the action of the neurotransmitter at the alpha receptor is blocked, the beta receptor is selectively stimulated or the action of the neurotransmitter at the beta receptor is blocked, so that it is determined that a change in the blood pressure of the patient has occurred.

Figure 2:
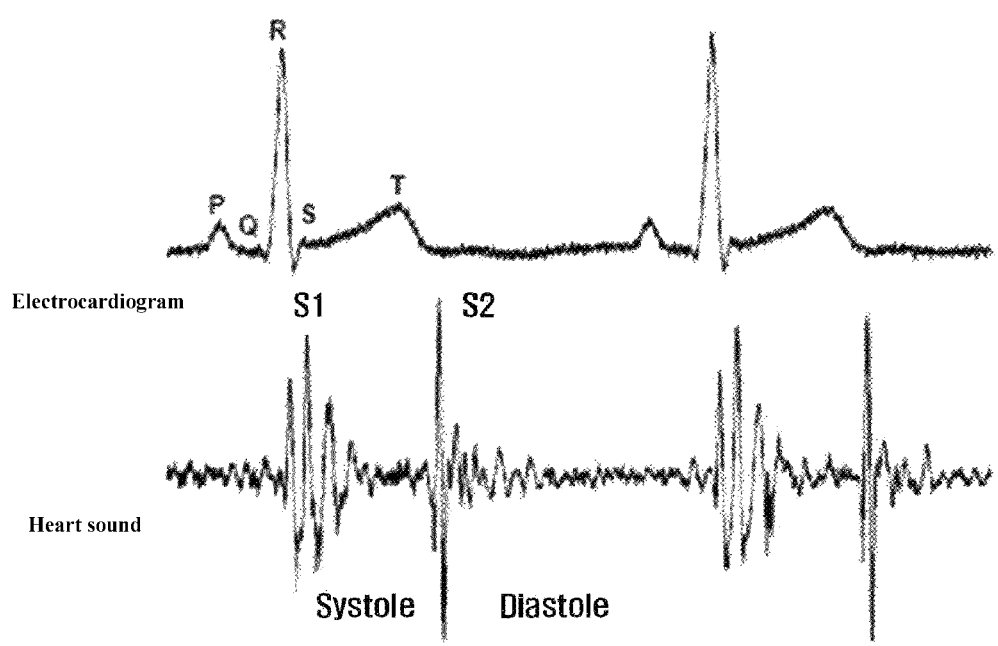

FIG. 2 is a diagram illustrating hemodynamic variables S1a and S2a according to some embodiments of the present disclosure.

Referring to FIG. 2, the hemodynamic variables S1a and S2a are derived from the first and second heart sounds, respectively.

The first heart sound S1 is a heart sound that is generated during systole corresponding immediately after the QRS wave of the electrocardiogram. The first heart sound S1, which is a closed sound generated while the atrioventricular valves (mitral valve and tricuspid valve) are closed, is generally generated immediately after the QRS wave, but is often generated before the QRS wave. The second heart sound S2 is a heart sound that is generated during diastole corresponding to a T-wave of the electrocardiogram. The second heart sound S2 is a closed sound generated while the semilunar valves (aortic valve and pulmonary artery valve) are closed. The first and second heart sounds S1 and S2 are distinguished from each other because the first heart sound S1 is relatively closed to the QRS wave time point. Although the waveform height of the first heart sound S1 is higher than that of the second heart sound S2, this differs depending on the measurement position of the heart sound.

The hemodynamic variables S1a and S2a are derived from the first amplitude of the first heart sound S1 and the second amplitude of the second heart sound S2, respectively. The S1a and S2a derived in this manner serve as quantitative surrogate markers of indexes on myocardial contractile force and vascular resistance. As will be described later, the relative change amounts of S1a and S2a quantitatively reflect the total change amounts of the indexes on myocardial contractile force and vascular resistance.

Figure 3:
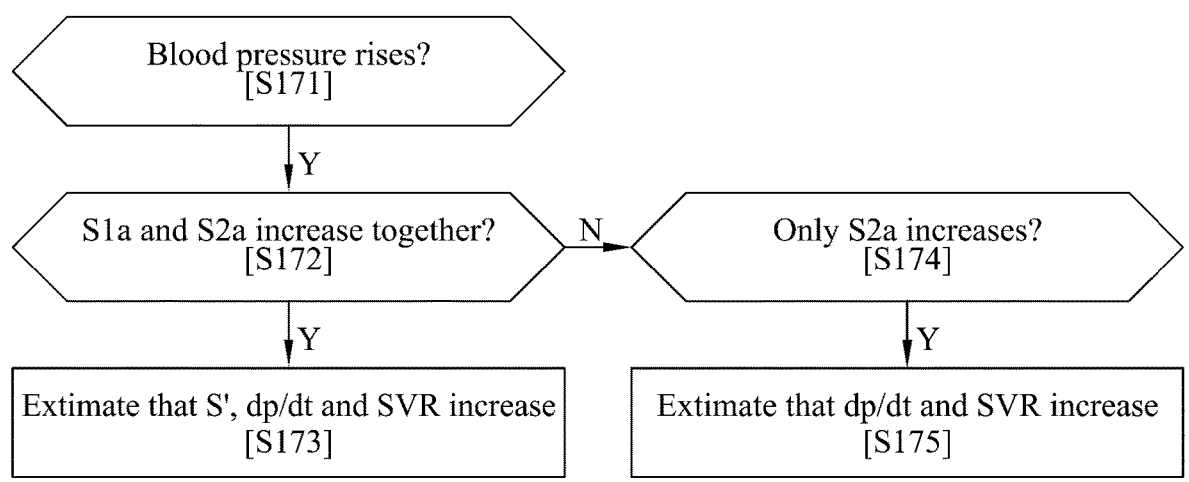
FIG. 3 is a flowchart illustrating detailed operations of estimating a change amount in a table for estimating change amounts of indexes related to myocardial contractile force and vascular resistance when a blood pressure of a patient increases.
Figure 4:
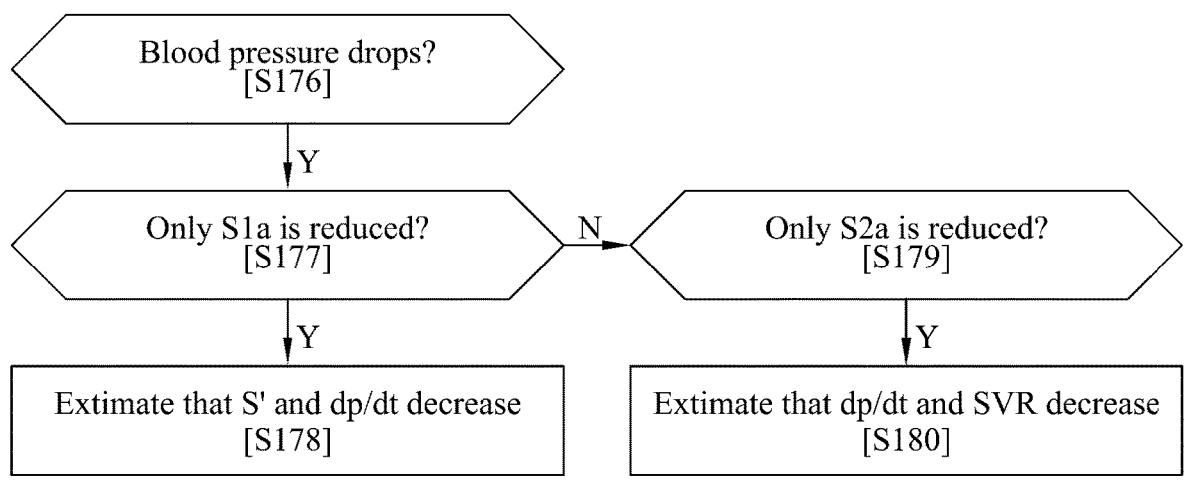
FIG. 4 is a flowchart illustrating detailed operations of estimating a change amount in a table for estimating change amounts of indexes related to myocardial contractile force and vascular resistance when the blood pressure of the patient decreases.

FIG. 3 is a flowchart illustrating detailed operations of estimating a change amount in a table for estimating change amounts of indexes related to myocardial contractile force and vascular resistance when the blood pressure of a patient increases, and FIG. 4 is a flowchart illustrating detailed operations of estimating a change amount in the table for estimating the change amounts of the indexes related to myocardial contractile force and vascular resistance when the blood pressure of the patient decreases.

Referring to FIG. 3, in operation S171, it is determined whether the blood pressure of the patient rises at least by a predetermined reference value of blood pressure rising. For example, the predetermined reference value of blood pressure rising is set to a predetermined value within a range of 15 to 30% increased relative to the normal standard blood pressure, but the embodiments are not limited thereto. In this case, the standard blood pressure means about 120 mmHg for systolic blood pressure and about 90 mmHg for mean arterial pressure.

Next, in operation S172, it is determined whether S1a and S2a increase together while the blood pressure of the patient rises. Then, when S1a and S2a increase together, it is estimated in operation S173 that S', dp/dt and SVR increase corresponding to each quantitative correlation.

In this case, the increase of each index means an increase of more than the reference change amount. Therefore, when any index does not change by more than the reference change amount, the index is treated as unchanged. The reference change amount is predetermined independently of each other for each index. By estimating the change amounts of S', dp/dt and SVR as described above, the cause of blood pressure increase and decrease is determined as the effect of alpha and beta actions.

Meanwhile, when S1a and S2a do not increase together, in operation S174, it is determined whether only S2a increases. Then, when only S2a increases, in operation S175, it is estimated that S' does not change above the reference change amount (i.e., S' does not change significantly), and dp/dt and SVR increase corresponding to each quantitative correlation. By estimating the change amounts of S', dp/dt and SVR as described above, the cause of blood pressure increase and decrease of the patient may be determined as the effect of the alpha action.

Referring to FIG. 4, in operation S176, it is determined whether the blood pressure of a patient drops equal to or lower than a predetermined drop reference blood pressure value. For example, the drop reference blood pressure value is set to a predetermined value within a range of 15 to 30% decreased relative to the normal standard blood pressure, but the embodiments are not limited thereto.

Next, in operation S177, it is determined whether only S1a decreases while the blood pressure of the patient decreases. Then, when only S1a decreases, in operation S178, it is estimated that S' and dp/dt decrease corresponding to each quantitative correlation and SVR does not change equal to or more than the reference change amount. In this case, the decrease of each index means a decrease of more than the reference change amount. Therefore, when any index does not change by more than the reference change amount, the index is treated as unchanged. The reference change amount is predetermined independently of each other for each index. By estimating the change amounts of S', dp/dt and SVR as described above, the cause of blood pressure increase and decrease is determined as an effect of beta blockage.

Meanwhile, when only S1a does not decrease, in operation S179, it is determined whether only S2a decreases. Then, when only S2a decreases, in operation S180, it is estimated that S' does not change beyond the reference change amount, and dp/dt and SVR decrease corresponding to each quantitative correlation. By estimating the change amounts of S', dp/dt and SVR as described above, the cause of blood pressure increase and decrease of the patient is determined as the effect of the alpha blockage.

Table 1 illustrates a particular embodiment that estimates the change amounts of the indexes on myocardial contractile force and vascular resistance based on increasing or decreasing of the blood pressure of a patient, the change amounts of S1a and S2a, and determines the cause of the change in blood pressure based on the estimation result.

In the first case of Table 1, when the blood pressure increases while S1a increases by 50%, S2a increases by 25% due to specific stimulation (drug administration, external stimulation, and the like), it is estimated that S' increases by 20% and dp/dt increases by 50%. Accordingly, it is determined that this is due to the effect of alpha and beta actions acting simultaneously on cardiac contractile force and peripheral vascular resistance.

In the second case of Table 1, when S1a is unchanged and the blood pressure increases together while S2a increases by 25%, it is estimated that dp/dt increases by 25% and SVR increases by 12%. Accordingly, it is determined that this is due to the effect of alpha action.

In the third case of Table 1, When S1a decreases by 50%, S2a and the blood pressure drops together while S2a is unchanged, it is estimated that S' decreases by 20% and dp/dt decreases by 25%. Accordingly, it is determined that this is due to the effect of beta blockage.

In the fourth case of Table 1, when S1a is unchanged and the blood pressure decreases together while S2a decreases by 25%, it is estimated that dp/dt decreases by 25% and SVR decreases by 12%. Accordingly, it is determined that this is due to the effect of alpha blockage.

As cases of administering a cardiovascular agonist, Table 2 illustrates an experimental example in which various indexes on myocardial contractile force and vascular resistance and changes in S1a and S2a were observed when ephedrine of 10 mg as alpha and beta agonist was administered, Table 3 illustrates an experimental example in which various indexes on myocardial contractile force and vascular resistance and changes in S1a and S2a were observed when esmolol of 25 mg as beta-blocker was administered, and Table 4 illustrates an experimental example in which various indexes on myocardial contractile force and vascular resistance and changes in S1a and S2a were observed when phenylephrine of 100 mcg as the alpha agonist was administered. In order to determine the cause of the change in blood pressure, the above-described agents causing the change in blood pressure were administered and the response after the administration was examined.

TABLE 2

| Classification | Before administration | After administration | P-value |
|---|---|---|---|
| SBP (mmHg) | 109.6 ± 13.2 | 139.3 ± 14.0 | <0.001 |
| SVR (dyne · sec/cm$^5$) | 719.4 ± 199.2 | 892.6 ± 250.2 | 0.011 |
| dp/dt (mmHg/s) | 725.2 ± 73.8 | 1065.5 ± 217.6 | 0.001 |
| S' | 9.7 ± 2.1 | 11.3 ± 2.7 | 0.014 |
| RRI (ms) | 652 ± 70 | 625 ± 90 | 0.029 |
| S1a (au) | 27.6 ± 12.6 | 43.7 ± 24.9 | 0.012 |

TABLE 1

| Blood pressure change | Change amount of S1a and S2a | Estimation of change amounts of S', dp/dt, SVR | Cause |
|---|---|---|---|
| Blood pressure rise | 50% increase in S1a<br>25% increase in S2a | 20% increase in S'<br>50% increase in dp/dt | Alpha and beta action |
| Blood pressure rise | No change in S1a<br>25% increase in S2a | 25% increase in dp/dt<br>12% increase in SVR | Alpha action |
| Blood pressure drop | 50% decrease in S1a<br>No change in S2a | 20% decrease in S'<br>25% decrease in dp/dt | Beta blockage |
| Blood pressure drop | No change in S1a<br>25% decrease in S2a | 25% decrease in dp/dt<br>12% decrease in SVR | Alpha blockage |

TABLE 2-continued

| Classification | Before administration | After administration | P-value |
|---|---|---|---|
| S2a (au) | 17.7 ± 8.1 | 22.6 ± 9.2 | 0.004 |
| S12_R | 1.79 ± 0.83 | 2.06 ± 0.84 | 0.209 |

TABLE 3

| Classification | Before administration | After administration | P-value |
|---|---|---|---|
| SBP (mmHg) | 136.1 ± 16.8 | 124.4 ± 13.2 | <0.001 |
| SVR (dyne · sec/cm$^5$) | 776.4 ± 256.1 | 750.8 ± 251.0 | 0.062 |
| dp/dt (mmHg/s) | 1051.5 ± 233.4 | 804.3 ± 151.1 | <0.001 |
| S' | 13.7 ± 4.4 | 10.2 ± 2.1 | 0.011 |
| RRI (ms) | 598 ± 96 | 700 ± 95 | <0.001 |
| S1a (au) | 49.3 ± 20.3 | 27.5 ± 9.3 | 0.001 |
| S2a (au) | 19.6 ± 5.5 | 21.1 ± 5.4 | 0.162 |
| S12_R | 2.6 ± 0.91 | 1.4 ± 0.38 | 0.001 |

TABLE 4

| Classification | Before administration | After administration | P-value |
|---|---|---|---|
| SBP (mmHg) | 93.7 ± 13.2 | 111.5 ± 13.8 | 0.014 |
| SVR (dyne · sec/cm$^5$) | 452.7 ± 110.0 | 524.0 ± 132.2 | 0.007 |
| dp/dt (mmHg/s) | 585.1 ± 106.1 | 744.8 ± 95.3 | <0.001 |
| S' | 21.4 ± 12.0 | 19.2 ± 8.5 | 0.402 |
| RRI (ms) | 575 ± 141 | 528 ± 197 | 0.384 |
| S1a (au) | 33.6 ± 20.8 | 31.4 ± 15.5 | 0.428 |
| S2a (au) | 14.29 ± 7.53 | 18.89 ± 8.14 | 0.016 |
| S12_R | 2.86 ± 1.73 | 4.18 ± 6.7 | 0.531 |

In contrast to the experimental results in Tables 2 and 3, overall considering that S1a and S2a increase together when ephedrine as alpha and beta agonist is administered, only S1a is significantly decreased when esmolol as beta blocker is administered, and any significant change does not occur in S1a unlike S2a when phenylephrine is administered as alpha agonist, it is confirmed that S1a represents the effect of beta action and S2a represents the effect of alpha action.

Through the experimental examples, it is confirmed that, when the change in blood pressure is accompanied by a change in myocardial contractile force, the decrease and increase of S1a is accompanied, and when there is no change in myocardial contractile force, only S2a changes.

Therefore, when S1a increases or decreases, the change in myocardial contractile force is suspected as a cause of blood pressure change, and when S2a increases or decreases, the change in vascular resistance is suspected as a cause of blood pressure change.

Through the above experiments and additional experiments, a table in which the change amounts of S', dp/dt and SVR corresponding to the change amounts of S1a and S2a are recorded, a formula or correlation coefficient for estimating the change amounts, and the like may be derived.

Figure 5:
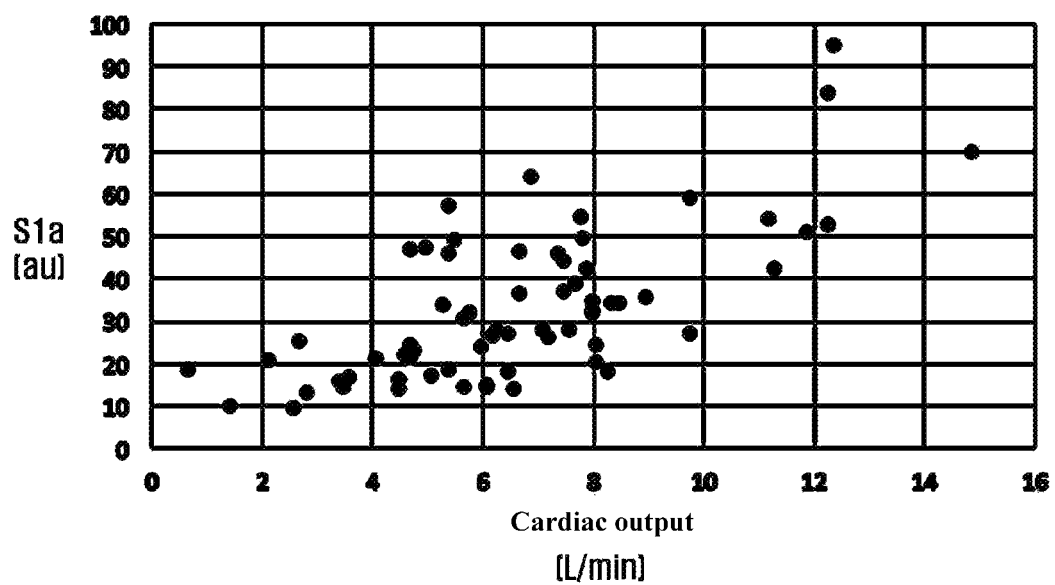
FIG. 5 is a graph illustrating a correlation between S1a and a cardiac output according to some embodiments of the present disclosure.
Figure 6:
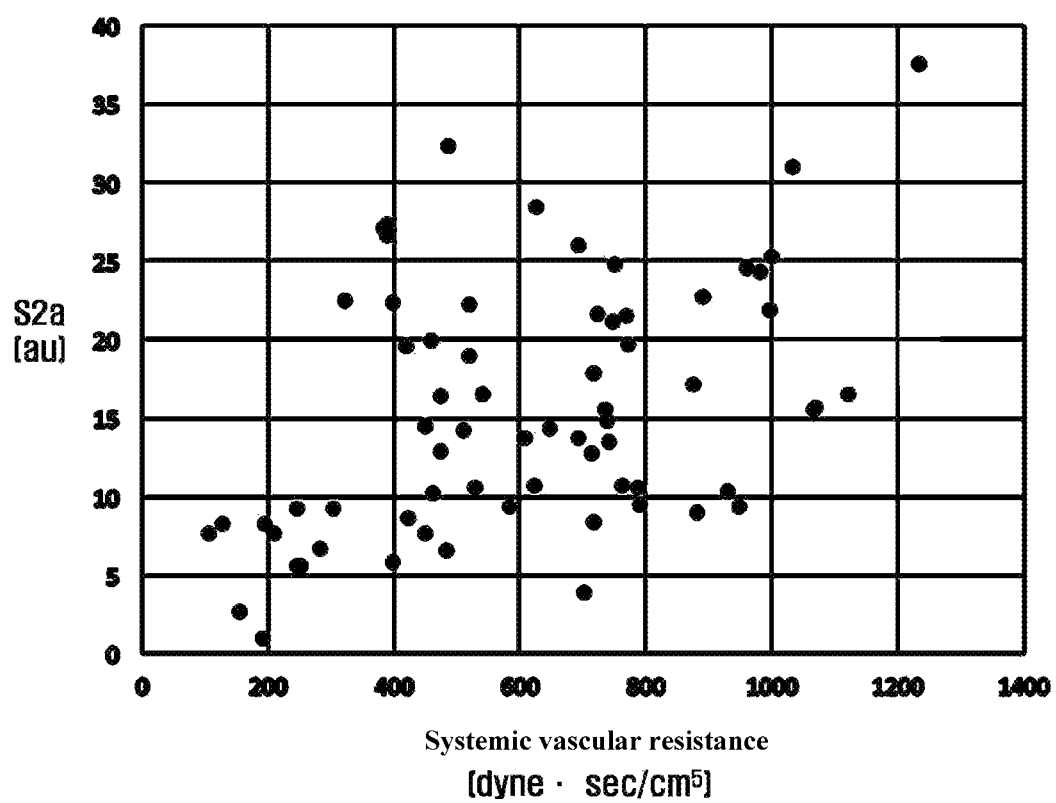
FIG. 6 is a graph illustrating a correlation between S2a and SVR according to some embodiments of the present disclosure.

FIG. 5 is a graph illustrating the correlation between S1a and a cardiac output according to some embodiments of the present disclosure. FIG. 6 is a graph illustrating the correlation between S2a and SVR according to some embodiments of the present disclosure.

Referring to FIGS. 5 and 6, S1a and the cardiac output, and S2a and SVR have a positive correlation. Because the cardiac output correlates with myocardial contractile force, S1a is positively correlated with myocardial contractile force.

Figure 7:
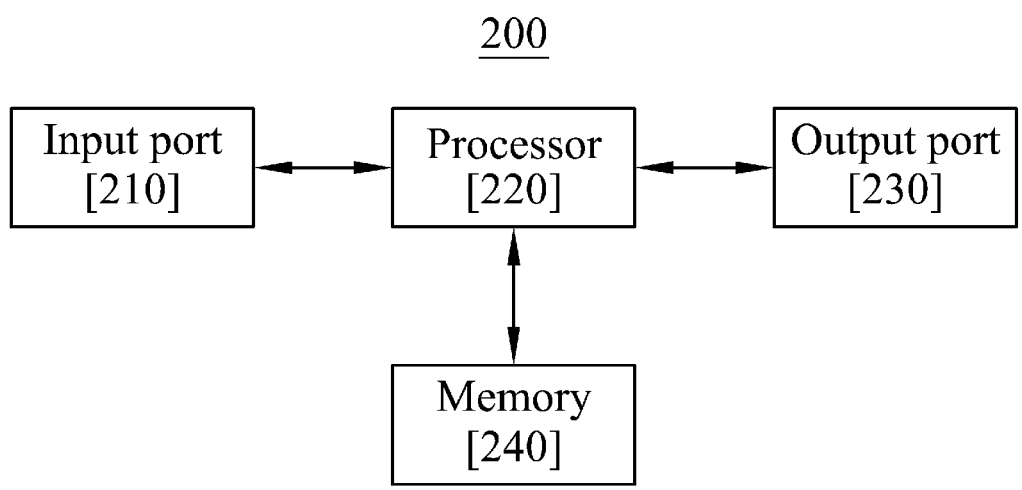
FIG. 7 is a block diagram illustrating an apparatus for performing a method of noninvasively determining a cause of a blood pressure change according to some embodiments of the present disclosure.

FIG. 7 is a block diagram illustrating an apparatus for performing a method of noninvasively determining a cause of a blood pressure change according to some embodiments of the present disclosure.

Referring to FIG. 7, an apparatus 200 includes an input port 210, a processor 220, an output port 230, and a memory 240.

The processor 220 performs a method of noninvasively determining a cause of a blood pressure change according to some embodiments of the present disclosure. In some embodiments, the processor includes, but is not limited to, a central processing unit (CPU), a graphics processing unit (GPU), an application specific integrated circuit (ASIC), a field programmable gate array (FPGA), etc., combinations thereof, or any other suitable computing device known in the art.

In some embodiments, the input port 210 is connected to a stethoscope to receive a heart sound, and the output port 230 outputs information about the cause of a blood pressure change.

The memory 240 stores a computer program in which a method of noninvasively determining a cause of a blood pressure change according to some embodiments of the present disclosure is implemented. In some embodiments, the memory includes, but is not limited to, random access memory (RAM), read only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, redundant array of independent disks (RAID) storage systems, or any other medium which can be used to store the desired information and which can be accessed by a computing device.

In some embodiments, the memory 240 stores a table in which the change amounts of indexes on myocardial contractile force and vascular resistance are recorded when alpha agonist, alpha blocker, beta agonist and beta blocker are administered, a table in which the change amounts of indexes on myocardial contractile force and vascular resistance according to the change amounts of S1a and S2a are recorded, and the like.

The operations of the method or algorithm described in connection with an embodiment of the inventive concept may be implemented directly in hardware, in a software module executed by hardware, or by a combination thereof. The software module may reside in a memory. The memory is, for example, a random access memory (RAM), read only memory (ROM), erasable programmable ROM (EPROM), electrically erasable programmable ROM (EEPROM), flash memory, hard disk, a removable disk, CD-ROM, or any form of computer readable recording medium well known in the art.

According to the inventive concept, as quantitative surrogate markers of indexes on myocardial contractile force and vascular resistance, the maximum amplitude of the first heart sound and the maximum amplitude of the second heart sound are obtained from the heart sound of a patient, and the change amounts of indexes on myocardial contractile force and vascular resistance are estimated based on the change amounts of the maximum amplitudes of the first and second heart sounds, so that, without using invasive arterial pressure measuring equipment and the like, through non-invasive test methods, the cardiovascular function of a patient may be estimated quickly, easily and precisely, and the cause of a blood pressure change may be determined based on at least one effect of alpha action, alpha blockage, beta action or beta blockage.

Effects of the present disclosure may not be limited to the above, and other effects of the present disclosure will be clearly understandable to those having ordinary skill in the art from the disclosures provided below together with accompanying drawings.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for noninvasively determining a cause of a blood pressure change, performed by a computer including a processor, the method comprising:
    obtaining heart sounds of a patient;
    obtaining a first maximum amplitude of a first heart sound and a second maximum amplitude of a second heart sound, from the obtained heart sounds;
    monitoring a first change in the first maximum amplitude and a second change in the second maximum amplitude;
    estimating a first change amount of a first index on a myocardial contractile force, a second change amount of a second index on the myocardial contractile force, and a third change amount of a third index on vascular resistance, based on increasing or decreasing of a blood pressure of the patient, a first change amount of the first maximum amplitude, and a second change amount of the second maximum amplitude of the second heart sound; and
    determining the cause of the blood pressure change of the patient as an effect of at least one of alpha action, alpha blockage, beta action and beta blockage, based on results of the estimation of the first change amount of the first index, the second change amount of the second index and the third change amount of the third index,
    wherein the first heart sound corresponds to a closed sound of a mitral valve or a tricuspid valve, and the second heart sound corresponds to a closed sound of an aortic valve or a pulmonary valve, and
    wherein
      the first index includes a systolic peak valve ring speed,
      the second index includes a change rate of ventricular pressure per hour, and
      the third index includes systemic vascular resistance.

2. The method of claim 1, wherein the obtaining the heart sounds comprises:
    obtaining the heart sounds from a stethoscope inserted into an esophagus of the patient or obtaining the heart sounds by processing an acoustic signal obtained from the patient.

3. The method of claim 1, wherein the obtaining the heart sounds comprises:
    amplifying a heart sound signal;
    converting an analog signal of the amplified heart sound signal into a digital heart sound data; and
    removing noise in the converted digital heart sound data by applying a filter to the converted digital heart sound data.

4. The method of claim 1, wherein the estimating comprises:
    estimating that the first, second and third indexes increase at least by a respective reference change amount corresponding to a respective quantitative correlation, when a first condition that the blood pressure of the patient rises at least by a predetermined reference value of blood pressure rising, and a second condition that the first and second maximum amplitudes increase at least by a predetermined reference value of maximum amplitude changing are satisfied.

5. The method of claim 4, wherein the determining comprises:
    determining the cause of the blood pressure change of the patient as the effect of the alpha action and the beta action, when it is estimated that the first, second and third indexes increase at least by the respective reference change amount corresponding to the respective quantitative correlation.

6. The method of claim 1, wherein the estimating comprises:
    estimating that the first index does not change at least by a reference change amount, and that the second and third indexes increase at least by a respective reference change amount corresponding to a respective quantitative correlation, when a first condition that the blood pressure of the patient rises at least by a predetermined reference value of blood pressure rising, a second condition that the first maximum amplitude does not change at least by a predetermined reference value of maximum amplitude changing, and a third condition that the second maximum amplitude increases at least by the predetermined reference value of maximum amplitude changing are satisfied.

7. The method of claim 6, wherein the determining comprises:
    determining the cause of the blood pressure change of the patient as the effect of the alpha action, when it is estimated that the first index does not change at least by the reference change amount, and that the second and third indexes increase at least by the respective reference change amount corresponding to the respective quantitative correlation.

8. The method of claim 1, wherein the estimating comprises:
    estimating that the first and second indexes decrease at least by a respective reference change amount corresponding to a respective quantitative correlation, and that the third index does not change at least by a reference change amount, when a first condition that the blood pressure of the patient drops equal to or lower less than a predetermined drop reference blood pressure value, a second condition that the first maximum amplitude decreases at least by a predetermined reference value of maximum amplitude changing, and a third condition that the second maximum amplitude does not change at least by the predetermined reference value of maximum amplitude changing are satisfied.

9. The method of claim 8, wherein the determining comprises:
    determining the cause of the blood pressure change of the patient as the effect of the beta action, when it is estimated that the first and second indexes decrease at least by the respective reference change amount corresponding to the respective quantitative correlation, and that the third index does not change at least by the reference change amount.

10. The method of claim 1, wherein the estimating comprises:
estimating that the first index does not change at least by a reference change amount, and that the second and third indexes decrease at least by a respective reference change amount corresponding to a respective quantitative correlation, when a first condition that the blood pressure of the patient drops equal to or lower than a predetermined drop reference blood pressure value, a second condition that the first maximum amplitude does not change at least by a predetermined reference value of maximum amplitude changing, and a third condition that the second maximum amplitude decreases at least by the predetermined reference value of maximum amplitude changing are satisfied.

11. The method of claim 10, wherein the determining comprises:
determining the cause of the blood pressure change of the patient as the effect of the alpha blockage, when it is estimated that the first index does not change at least by the reference change amount, and that the second and third indexes decrease at least by the respective reference change amount corresponding to the respective quantitative correlation.

12. An apparatus for performing a method for noninvasively determining a cause of a blood pressure change, the apparatus comprising:
an input port configured to receive heart sounds;
a processor configured to perform operations including:
obtaining a first maximum amplitude of a first heart sound and a second maximum amplitude of a second heart sound, from the received heart sounds;
monitoring a first change in the first maximum amplitude and a second change in the second maximum amplitude;
estimating a first change amount of a first index on a myocardial contractile force, a second change amount of a second index on the myocardial contractile force, and a third change amount of a third index on vascular resistance, based on increasing or decreasing of a blood pressure of a patient, a first change amount of the first maximum amplitude, and a second change amount of the second maximum amplitude of the second heart sound; and
determining the cause of the blood pressure change of the patient as an effect of at least one of alpha action, alpha blockage, beta action and beta blockage, based on results of the estimation of the first change amount of the first index, the second change amount of the second index and the third change amount of the third index,
wherein the first heart sound corresponds to a closed sound of a mitral valve or a tricuspid valve, and the second heart sound corresponds to a closed sound of an aortic valve or a pulmonary valve;
a memory configured to store instructions for performing the operations by the processor; and
an output port configured to output information about the determined cause of the blood pressure change, and
wherein
the first index includes a systolic peak valve ring speed,
the second index includes a change rate of ventricular pressure per hour, and
the third index includes systemic vascular resistance.

13. A computer program which is coupled to a processor and stored in a medium, the computer program including instructions for performing:
obtaining heart sounds of a patient;
obtaining a first maximum amplitude of a first heart sound and a second maximum amplitude of a second heart sound, from the obtained heart sounds;
monitoring a first change in the first maximum amplitude and a second change in the second maximum amplitude;
estimating a first change amount of a first index on a myocardial contractile force, a second change amount of a second index on the myocardial contractile force, and a third change amount of a third index on vascular resistance, based on increasing or decreasing of a blood pressure of the patient, a first change amount of the first maximum amplitude, and a second change amount of the second maximum amplitude of the second heart sound; and
determining a cause of the blood pressure change of the patient as an effect of at least one of alpha action, alpha blockage, beta action and beta blockage, based on results of the estimation of the first change amount of the first index, the second change amount of the second index and the third change amount of the third index,
wherein the first heart sound corresponds to a closed sound of a mitral valve or a tricuspid valve, and the second heart sound corresponds to a closed sound of an aortic valve or a pulmonary valve, and
wherein
the first index includes a systolic peak valve ring speed,
the second index includes a change rate of ventricular pressure per hour, and
the third index includes systemic vascular resistance.

* * * * *